United States Patent [19]
Horn et al.

[11] Patent Number: 5,817,854
[45] Date of Patent: Oct. 6, 1998

[54] PROCESS FOR THE PREPARATION OF ORGANOCARBONOYLOXYSILANES

[75] Inventors: Michael Horn; Albert-Johannes Frings; Peter Jenkner; Jaroslaw Monkiewicz; Claus-Dietrich Seiler, all of Rheinfelden; Burkhard Standke, Loerrach; Bertram Trautvetter, Rheinfelden, all of Germany

[73] Assignee: Huels Aktiengesellschaft, Marl, Germany

[21] Appl. No.: 978,025

[22] Filed: Nov. 25, 1997

[30] Foreign Application Priority Data

Nov. 27, 1996 [DE] Germany .................. 196 49 027.8

[51] Int. Cl.⁶ ...................................................... C07F 7/08
[52] U.S. Cl. .............................................................. 556/442
[58] Field of Search ................................................ 556/442

[56] References Cited

U.S. PATENT DOCUMENTS 3,974,198  8/1976  Ashby ...................................... 556/442

*Primary Examiner*—Paul F. Shaver
*Attorney, Agent, or Firm*—Oblon, Spivak, McClelland, Maier & Neustadt, P.C.

[57] ABSTRACT

Organocarbonoyloxysilanes are prepared by reacting an organochlorosilane with a carboxylic acid in a first step which liberates HCl, removing the HCl which is formed, reacting the reaction mixture from the first step with a carboxylic acid anhydride in a second reaction step, the first and/or second reaction steps being conducted in the presence of a catalyst, and isolating the resulting organocarbonoyloxysilane product from the reaction mixture.

16 Claims, 1 Drawing Sheet

PROCESS FOR THE PREPARATION OF ORGANOCARBONOYLOXYSILANES

BACKGROUND OF THE INVENTION

FIELD OF THE INVENTION

The present invention relates to a process for the preparation of organocarbonoyloxysilanes.

DESCRIPTION OF THE BACKGROUND

Carbonoyloxysilanes have found diverse use in the chemical industry. For example, they are suitable as cross-linking silicon compounds in the preparation of compositions which can be stored in the absence of water and can be cured at room temperature upon exposure to moisture. Examples of these compounds include methyl-, ethyl- and propyl-tris(ethanoyloxy) silane.

For such silanes and their preparation processes, the requirements with respect to profitability and purity of the products, and also with respect to residual chlorine contents, have increased to an extreme degree in recent times.

Essentially two procedures are used for the preparation of carbonoyloxysilanes on industrially economical scales.

One procedure uses the reaction of organochlorosilanes with carboxylic acids to give the corresponding organocarbonoyloxysilanes. This procedure is practiced by both batch and continuous procedures. Batch preparations require the presence of an inert solvent and long reaction times, in order to reduce the residual contents of acid chlorine to values below 100 ppm (U.S. Pat. No. 2,437,073, U.S. Pat. No. 2,866,800, U.S. Pat. No. 3,974,198, GB 814 011). Continuous reactions of organochlorosilanes with carboxylic acids are disclosed in the publications DE 2 801 780, DE 3 221 702, EP 0 003 317, U.S. Pat. No. 4,332,956, U.S. Pat. No. 4,329,484. If minimal excess amounts of carboxylic acid, based on the amounts of organochlorosilane employed, are used, contents of acid chloride on the order of up to 50 ppm remain. Only the use of large excesses of carboxylic acid of the order of 50% enables the contents of acid chloride to be reduced to values of less than 1 ppm at siloxane contents which can be tolerated.

The procedure for the preparation of carbonoyloxysilanes on an industrial scale in which the carboxylic acid is employed as such is in general less profitable than the other procedure, which uses the reaction of organochlorosilane with carboxylic acid anhydrides to give the organocarbonoyloxysilane, with simultaneous formation of the corresponding carboxylic acid chloride. The reason for this resides essentially in the generally higher acquisition or starting substance costs for the carboxylic acid compared with the corresponding carboxylic acid anhydride.

FR 1 003 073 describes the batchwise and simultaneous preparation of carbonoyloxysilanes and carboxylic acid chlorides by reaction of organochlorosilanes with monocarboxylic acid anhydrides.

A continuous preparation procedure for carbonoyloxysilanes is disclosed in EP 0 509 213. Here, organochlorosilanes are reacted with carboxylic acid anhydrides in the presence of specific catalysts to give carbonoyloxysilanes and carbonoyl chlorides. The specific procedure enables the content of acid chlorine in the end products to be reduced from, for example, 800 ppm to 3 ppm.

The process in which the carboxylic acid anhydride is employed as a starting reactant is favored over the process in which a monocarboxylic acid is employed in view of the cheaper cost of, for instance, acetic anhydride over acetic acid. However, it cannot be ensured that the carboxylic acid chloride formed as a by-product can also be sold on the market in amounts corresponding to the main product, and as a result the economic advantage of the cost of favored starting substance can rapidly be dissipated.

The literature also describes procedures for the preparation of carbonoyloxysilanes by reaction of the corresponding organochlorosilanes with alkali metal carboxylates in the presence of large amounts of an inert diluent. These procedures are associated with the production of considerable amounts of salt. It, thus, is necessary to remove the target product from the reaction mixture by expensive washing processes. These procedures are not very practicable industrially, and also do not meet current economic and ecological requirements (U.S. Pat. No. 2,573,302, GB 640 834, DE 870 554, U.S. Pat. No. 2,537,073, U.S. Pat. No. 2,866,800).

A need, therefore, continues to exist for a method of preparing carbonoylsilanes by an industrial practical process which also meets current economic and ecological requirements.

SUMMARY OF THE INVENTION

Accordingly, one object of the present invention is to provide an economic and simple process for the preparation of organocarbonoyloxysilanes.

Another object of the present invention is to provide a process by which carboxylic acid chloride produced in the reaction can be consumed thereby eliminating disposal problems.

Briefly, these objects and other objects of the present invention as hereinafter will become more readily apparent can be achieved in a process for preparing organocarbonoyloxysilanes by reacting an organochlorosilane with a carboxylic acid in a first step which liberates HCl, removing the HCl which is formed, reacting the remaining reaction mixture with a carboxylic acid anhydride in a second reaction step, the first and/or second reaction steps being conducted in the presence of a catalyst, and isolating the resulting organocarbonoyloxysilane product from the reaction mixture.

BRIEF DESCRIPTION OF THE DRAWING

A more complete appreciation of the invention and many of the attendant advantages thereof will be readily obtained as the same becomes better understood by reference to the following detailed description when considered in connection with the accompanying drawing, wherein.

DETAILED DESCRIPTION OF THE PREFERRED EMBODIMENTS

Figure 1:
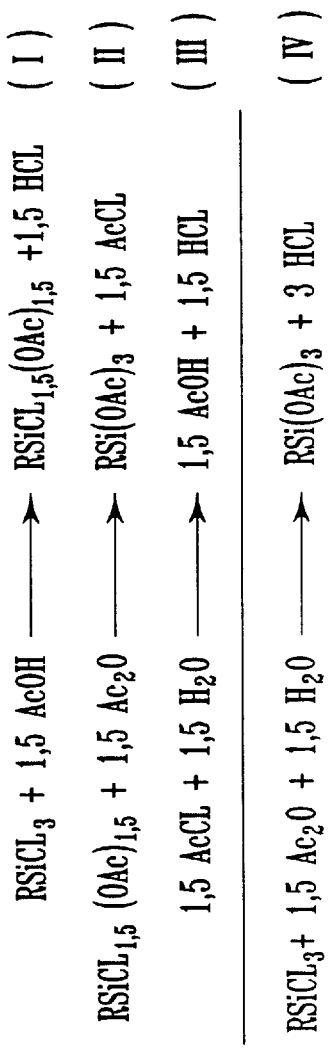
FIG. 1 shows the sum of reactions of the present process.

In the process according to the invention, the first and/or second reaction step is (are) preferably carried out in the presence of an inert diluent. Pentane, hexane, benzene, toluene and trichloroethylene, for example, are suitable diluents. The first and/or second reaction step is (are) furthermore conducted in the presence of at least one catalyst. A nitrogen-containing catalyst is preferably employed for this purpose, particularly preferably a carboxylic acid amide, for example, N,N-dimethylformamide. The catalyst is employed in an amount of up to 500 ppm by weight, preferably in amounts of 20 to 100 ppm by weight, based on the amount of organochlorosilane employed in the process.

In carrying out the present process, half of the chlorine present in the organochlorosilane reacts with the corresponding stoichiometric amount of carboxylic acid in the first reaction step. In the second reaction step, the carboxylic acid anhydride is preferably initially introduced into a reaction vessel, and then the reaction mixture obtained in the first reaction step is added thereto. The reaction which occurs in the second step is brought to completion, and the carboxylic acid chloride product which forms is continuously removed. However, it is also possible for the reaction mixture from the first reaction step to be initially introduced into the reaction vessel and then for the carboxylic acid anhydride to be added. The product mixture is preferably worked up, i.e. essentially the carboxylic acid chloride formed in the second reaction step is removed, by distillation techniques.

As a rule, the first and/or second reaction step of the present process is (are) carried out at a temperature in the range from 50° to 110° C. In order to achieve better thorough mixing of the reaction mixtures, the first and/or second reaction step(s) can be carried out with stirring. The reactions of the invention are in general carried out under normal pressure, but they can also be carried out under reduced pressure or increased pressure. Working up of the product mixture resulting from the second reaction step is suitably carried out under reduced pressure, preferably at a pressure of 1000 to 5 mbar.

In the process, the carboxylic acid anhydride is preferably employed in an amount such that the amount of carboxylic acid chloride produced during work-up of the product mixture can be employed in the form of the carboxylic acid in the first reaction step of the process, the HCl acid being formed by the hydrolysis of the acid chloride with water followed by removal of the hydrogen chloride.

Vinyl-, methyl-, ethyl-, propyl- or phenyltrichlorosilanes, dimethyldichlorosilane and 2-chloroethylmethyldichlorosilane, in particular, are employed in the process of the invention.

The carbonoyloxysilanes prepared by the process have the formula:

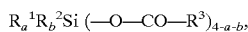

wherein a can have the value 3, 2 or 1 and b is 1 or 0 and a+b≦3. Those compounds in which a=1 and b=0 are preferred.

$R^1$ and $R^2$ are suitably hydrogen or saturated or unsaturated hydrocarbon radicals which have in each case 1 to 10 carbon atoms and can optionally contain functional groups, for example halogen, which are not attacked under the given reaction conditions, and are cyclic saturated or unsaturated hydrocarbon radicals having 6 carbon atoms, $R^1$ and $R^2$ can be identical or different, and $R^3$ the, in particular, is hydrogen, methyl, ethyl or propyl.

The following compounds are particularly preferred products of the invention:

vinyl-tris(ethanoyloxy)silane, ethyl-tris(ethanoyloxy) silane, methyl-tris(ethanoyloxy)silane, propyl-tris (ethanoyloxy)silane, dimethyl-bis(ethanoyloxy)silane and phenyl-tris(ethanoyloxy)silane.

FIG. 1 is a diagram of the equations of the present process. In equation (I), the reaction of an organotrichlorosilane with acetic acid is shown, with hydrogen chloride being removed, in a first step. In a second step, i.e., equation (II), the reaction mixture present from the first stage is reacted with acetic anhydride producing the organotriacetoxysilane product and acetyl chloride by-product, which is suitably separated from the product. Hydrolysis of the acetyl chloride present and recycling of the carboxylic acid into the process is then preferably carried out, as shown in reaction equations (III) and (I). From the total equation (IV), it further becomes clear that, in this preferred embodiment, the process of the invention allows a particularly economic operation by the use of the carboxylic acid anhydride with addition of water. An advantage of the present process is, therefore, elimination of carboxylic acid chloride as a product which must be sold or disposed or reused.

Furthermore, the residual content of acid chloride in the product can be removed from the carbonoyloxysilane product by optional stepwise addition of metal carboxylate and removal of the metal chlorides formed. (Reference is made to copending applications, Attorney Docket Nos. 689-724-0 and 689-730-0 which also describe such metal carboxylate treatment.) Cl impurity contents of <1 ppm by weight in the carbonoyloxysilane product can be achieved with only comparatively small amounts of metal salts being produced.

Moreover, no noticeable amounts of solvent are necessary in the present process. The process of the invention or component steps of the process can furthermore be carried out continuously.

Having generally described this invention, a further understanding can be obtained by reference to certain specific examples which are provided herein for purposes of illustration only and are not intended to be limiting unless otherwise specified.

EXAMPLES

Example 1

A 800 g (4.5 mol) amount of n-propyltrichlorosilane, 350 g of hexane and 0.1 ml of N,N-dimethylformamide are initially introduced into a standard glass reactor of 2 l capacity with a magnetic stirrer, a dropping funnel, a water condenser and a heat exchanger cooled to −40° C. via a cryomat. The reaction mixture is heated in an oil bath of 100° C., and the metering in of 402 g (6.7 mol) of acetic acid is started at an internal temperature of 60° C. The hydrogen chloride liberated is removed via the condenser combination. The addition is ended after 90 minutes, after which the temperature of the heating bath is reduced to 80° C. The mixture is subsequently boiled for about an additional hour and then cooled to 30° C.

A 1150 g (11.3 mol) amount of acetic anhydride is initially introduced at 65° C. into a second apparatus comprising a 2 l flask with a magnetic stirrer, an 80 cm column of 25 mm diameter, packed with ceramic saddle bodies, and a condenser combination as described for the first reactor, as well as a dropping funnel. About 30% of the mixture obtained in the first reaction step is first added via the dropping funnel, with continued stirring and heating with an oil bath regulated at 80° C. The acetyl chloride which forms is removed by distillation and collected in an ice-cooled receiver. Further reaction mixture is metered in synchronously. The rate of distillation subsides during this phase, after which the distillation receiver is emptied and the pressure of the unit is reduced to finally 200 mbar with a water jet pump. After a further change of fraction, the pressure of the unit is reduced further down to 35 mbar, until the distillation stops. The contents of the flask are now cooled to ambient temperature.

A sample is taken and is analyzed by gas chromatography and for acid chloride content. Residual contents of 9.5% of acetic anhydride and 135 ppm of acid chloride are found content.

The weights from distillation are determined as 350 g of acetic anhydride, which can be employed again, and 878 g of a hexane/acetyl chloride mixture, which gives 402 g of acetic acid and 340 g of hexane after work-up by hydrolysis.

The 80 cm column is replaced by one of 15 cm length and the distillation is continued, using an oil vacuum pump. A 104 g amount of acetic anhydride and 1080 g of n-propyltriacetoxysilane, in addition to 30 g of distillation residue, are obtained as fractions. The n-propyltriacetoxysilane still contains 15 mg/kg of acid chloride, in addition to about 1.5% of oligomers.

Example 2

The apparatus as described in Example 1 is used in which 700 g (4.7 mol) of methyltrichlorosilane in 350 g of hexane and 420 g (7.0 mol) of acetic acid are reacted. The heating temperature is limited to 90° C. in this first stage and the metering time is lengthened to 120 minutes.

For the second stage, 1200 g (11.8 mol) of acetic anhydride are initially introduced into the reaction vessel and, in a reaction procedure as described in Example 1, a crude product containing 8% of acetic anhydride and 90 mg/kg of acid chloride is obtained. Upon distillation 375 g of acetic anhydride and 920 g of hexane/acetyl chloride are obtained. The latter gives 420 g of acetic acid and 340 g of hexane after hydrolysis and distillation.

A 82 g amount of acetic anhydride, 985 g of methyltriacetoxysilane and 30 g of distillation residue are obtained from the distillation.

Example 3

For a batch reaction on an industrial scale, a unit which comprises a 2000 l reactor equipped with a stirrer, condensers and receivers, and a further 2000 l reactor equipped with a stirrer, distillation column with distillate receivers and a vacuum device is used.

A 800 kg (4.9 kmol) amount of ethyltrichlorosilane, 350 kg of hexane and 50 ml of N,N-dimethylformamide are initially introduced into the first reactor. A 438 kg (7.3 kmol) amount of acetic acid is metered in at the boiling point of the hexane over 3 hours, and the mixture is subsequently boiled for a further 2 hours. The hydrogen chloride liberated is removed.

A sample taken subsequently and measured by gas chromatography shows that the residual acetic acid content is less than 1%. The content of siloxanes is also indicated as about 1%.

The second reactor is charged with 1250 kg (12.2 kmol) of acetic anhydride and heated up to 65° C. About one third of the reaction mixture from the first reactor is added to the second reactor, and the temperature is increased until acetyl chloride is removed by distillation at the top of the column. At this point, the feed of additional reaction mixture from the first reactor is started. During this operation, heating is increased according to the progress of the reaction, until a bottom temperature of 90° C. is reached. The pressure is then reduced until, after the end of the metering of material, only the excess acetic anhydride is available for removal. This excess anhydride is also removed under reduced pressure at a maximum bottom temperature of 90° C.

At the end of the reaction, 1202 kg of crude ethyltriacetoxysilane, which contains about 5% of acetic anhydride, about 922 kg of a mixture of acetyl chloride and hexane and 437 kg of recovered acetic anhydride, which is employed again in the next batch, are obtained.

The acetyl chloride/hexane mixture is subjected to hydrolytic work-up and the hexane is separated by distillation from the acetic acid formed by this procedure. A 438 kg amount of acetic acid and 344 kg of hexane are recovered.

The resulting distillates of hexane, acetic acid and acetic anhydride can be recycled back into the process without further purification.

A 1110 kg amount of ethyltriacetoxysilane, 57 kg of acetic anhydride and 35 kg of distillation residue are obtained during the distillation. The ethyltriacetoxysilane is produced having a content of acid chloride of <10 ppm.

Example 4

Ethyltriacetoxysilane is prepared in a batch process as described in Example 3, and before distillation, the content of acid chloride is determined as 54 mg/kg. Thereafter, 150 g of sodium acetate are added as a suspension in 700 ml of acetic anhydride and the mixture is subjected to fractional distillation. The amounts of distillate obtained remain practically unchanged, but the determination of the acid chloride in the product of the main runnings gives a value of <2 mg/kg.

The disclosure of German priority application 196 49 027.8 filed Nov. 27, 1996 is hereby incorporated by reference.

Obviously numerous modifications and variations of the present invention are possible in light of the above teachings. It is, therefore, to be understood that within the scope of the appended claims, the invention may be practiced otherwise than as specifically described herein.

What is claimed as new and desired to be secured by Letters Patent of the United States is:

1. A process for the preparation of organocarbonoyloxysilanes, comprising:

reacting an organochlorosilane with a carboxylic acid in a first reaction step which liberates HCl;

removing the HCl which is formed;

reacting the reaction mixture of the first step with a carboxylic acid anhydride in a second reaction step, the first and/or second reaction steps being conducted in the presence of a catalyst; and isolating the resulting organocarbonoyloxysilane product from the reaction mixture.

2. The process as claimed in claim 1, wherein the first and/or second reaction step is (are) carried out in the presence of an inert diluent.

3. The process as claimed in claim 1, wherein the first and/or second reaction step is (are) carried out in the presence of at least one catalyst.

4. The process as claimed in claim 3, wherein a nitrogen-containing catalyst is employed as the catalyst.

5. The process as claimed in claim 4, wherein a carboxylic acid amide is employed as the catalyst.

6. The process as claimed in claim 1, wherein the catalyst is employed in an amount of up to 500 ppm by weight, based on the amount of organochlorosilane employed.

7. The process as claimed in claim 1, wherein, in the first reaction step, half of the chlorine present in the organochlorosilane is reacted with the corresponding stoichiometric amount of carboxylic acid.

8. The process as claimed in claim 1, wherein, in the second reaction step, the carboxylic acid anhydride is initially introduced into the reaction vessel, the reaction mixture obtained in the first reaction step is added and the second reaction step is brought to completion with continuous removal of the carboxylic acid chloride formed.

9. The process as claimed in claim 1, wherein the carboxylic acid anhydride is employed in the second reaction step in an amount such that the amount of carboxylic acid chloride produced in the second reaction step can be employed again as the carboxylic acid in the first reaction step, after hydrolysis with water and removal of the hydrogen chloride formed.

10. The process as claimed in claim 1, wherein the process or component steps of the process is (are) carried out continuously.

11. The process as claimed in claim 2, wherein the inert diluent is pentane, hexane, benzene, toluene or trichloroethylene.

12. The process claimed in claim 5, wherein said catalyst is N,N-dimethylformamide.

13. The process as claimed in claim 1, wherein the first and second reaction steps are conducted at a temperature of from 50° to 110° C.

14. The process as claimed in claim 1, wherein the product organocarbonoyloxysilane product is isolated under a reduced pressure of 1000 to 5 mbar.

15. The process as claimed in claim 1, wherein the organochlorosilane is vinyl-, methyl-, ethyl-, propyl-, or phenyl-trichlorosilane, dimethyldichlorosilane or 2-chloroethylmethyldichlorosilane.

16. The process as claimed in claim 1, wherein the organocarbonoyloxysilane product has the formula:

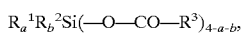

wherein a is 1, 2 or 3, b is 0 or 1, a+b≦3 and $R^1$ and $R^2$ are each hydrogen or saturated or unsaturated $C_{1-10}$-hydrocarboyl and $R^3$ hydrogen, methyl, ethyl or propyl.

* * * * *